United States Patent [19]

Eckstein et al.

[11] Patent Number: 4,812,650

[45] Date of Patent: Mar. 14, 1989

[54] GROWTH RATE MONITOR FOR MOLECULAR BEAM EPITAXY

[75] Inventors: James N. Eckstein, Cupertino; Christopher Webb, Los Altos; Shang-Lin Weng, Cupertino, all of Calif.

[73] Assignee: Varian Associates, Inc., Palo Alto, Calif.

[21] Appl. No.: 223,747

[22] Filed: Jul. 15, 1988

Related U.S. Application Data

[63] Continuation of Ser. No. 94,247, Sep. 8, 1987, abandoned.

[51] Int. Cl.[4] ............................................. G01N 21/00
[52] U.S. Cl. ................................... 250/307; 250/306; 156/601; 156/DIG. 103
[58] Field of Search ...................... 250/306, 307, 305; 156/601, DIG. 103; 437/8

[56] References Cited

U.S. PATENT DOCUMENTS 4,096,386 6/1978 Rempfer et al. ................... 250/306
4,332,833 6/1982 Aspnes et al. ...................... 156/601
4,575,462 3/1986 Dobson et al. ............. 156/DIG. 103

OTHER PUBLICATIONS

J. B. Theeten, "Analysis of a Surface Crystallography of a Solid: LEED and RHEED Techniques", Acta Electronica, 18, 1, 1975, pp. 39–45.

*Primary Examiner*—Carolyn E. Fields
*Assistant Examiner*—John A. Miller
*Attorney, Agent, or Firm*—Stanley Z. Cole; Kenneth L. Warsh; Gerald M. Fisher

[57] ABSTRACT

A light source with appropriate optics focusses light on the wafer surface during deposition, while a nearby collector is biased to collect photoemitted electrons from the growing surface. A pico ammeter can be used to convert the small oscillatory current detected to a substantial voltage signal which can be recorded or processed by computer or other sutiable device. The light must contain wavelengths at energies close to or greater than the energy of the photoemission threshold. The detected photoemitted electron signal has an oscillatory component occurring due to the growth of epitaxial layers. This oscillation has frequency $1/\tau$, where $\tau$ is the monolayer accumulation time.

24 Claims, 2 Drawing Sheets

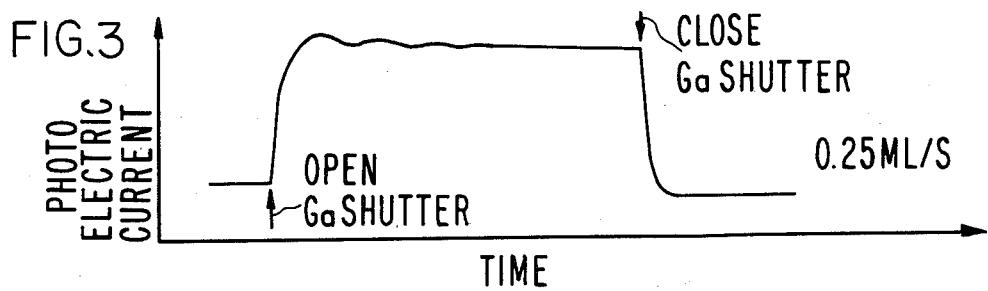
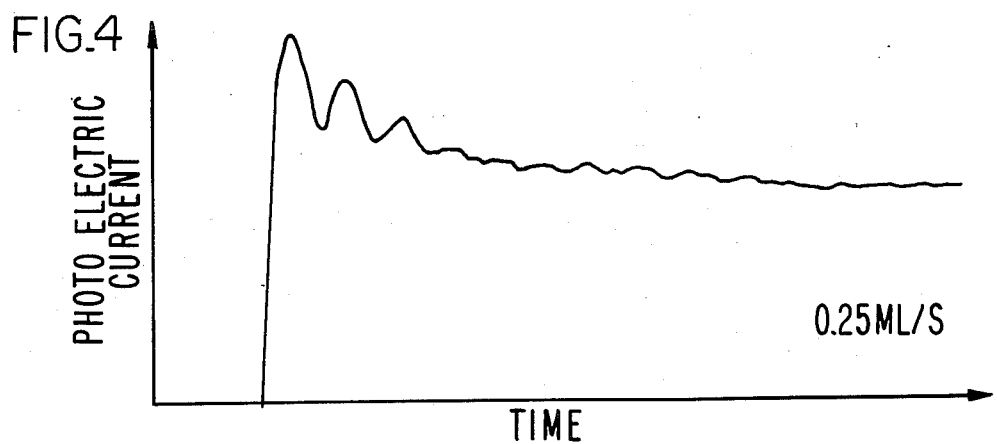
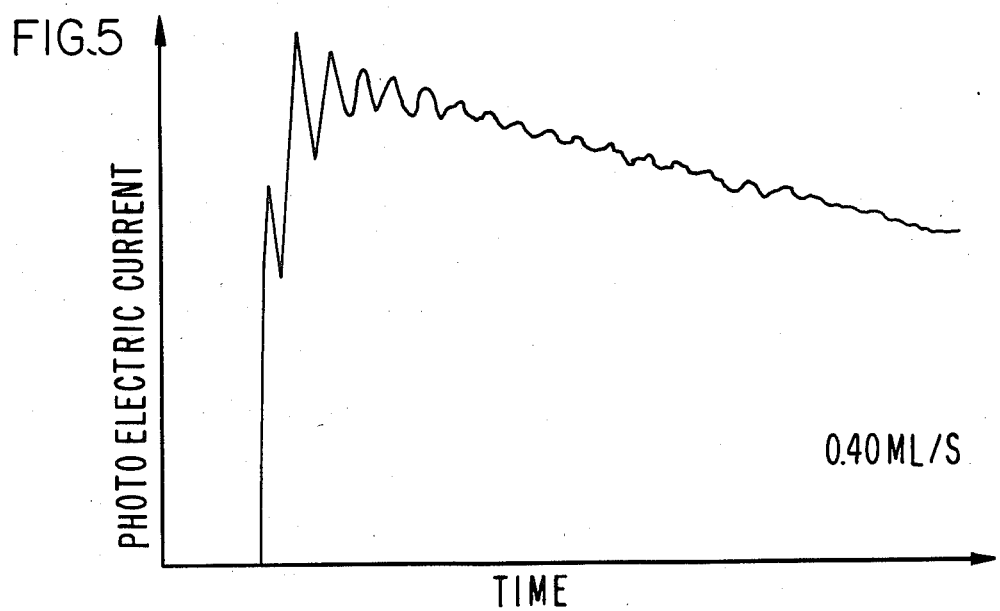

GROWTH RATE MONITOR FOR MOLECULAR BEAM EPITAXY

This application is a continuation, of application Ser. No. 094,247, filed 9/8/87, now abandoned.

FIELD OF THE INVENTION

This invention pertains to an apparatus and method for measuring the growth rate of a depositing layer in a molecular beam epitaxy apparatus, and in particular to an apparatus and method using photoelectron oscillation for measurement of growth rate.

BACKGROUND OF THE INVENTION

Growth rates in a molecular beam epitaxy system can be inferred from measured beam fluxes. In principle, this can be done during deposition by placing an ion gauge of some sort in the periphery of the beam. More typically, beam fluxes from effusion cells are measured prior to deposition and assumed to remain constant.

Actual growth rates of layers can be measured by noting the oscillations in Reflection High Energy Electron Diffraction (RHEED) pattern intensities as a function of time after growth is initiated. RHEED is ideally suited for analyzing growing layers since it does not involve apparatus which would tend to block the molecular beams. In particular, the study of RHEED intensity oscillations caused by the periodic variation in the density of monolayer terrace edges has uncovered many aspects of the layer by layer epitaxial growth process and has allowed precise determination of structures grown. (See: Cohen et al., *J. Vacuum Sci. Technol.*, A4, p.1251, 1986; Dobson et al., *J. Crys. Growth*, 81, p.1, 1987).

In the case of beam flux measurements, it is necessary to convert the flux into actual molecular layer growth rates. For many substances, evaporation from the growing wafer surface of one or more component is important and makes the correlation between growth rate and beam flux quite complicated and unusable.

RHEED intensity oscillations successfully circumvent this problem by actually measuring growth rates of molecular layers. However, to get stable RHEED patterns from which to measure intensity oscillations, the wafer must be mounted in a stationary position relative to the incident electron beam. This requires that the wafer not be rotating. However, due to nonuniformity in growth rates across the substrate position for all current source geometries highly non-uniform growth rate layer growth results without rotation. In fact, substrate rotation was introduced into MBE systems for just this reason. Thus, there is an inherent incompatibility between the needs of the RHEED measurement and the needs for layer uniformity.

An additional problem is the damage to the substrate which has been observed caused by the RHEED electron beam. Furthermore, RHEED is insensitive to some of the properties of the crystal surface which are important to an understanding of the nature of the crystal being grown.

OBJECTS OF THE INVENTION

An object of the invention is to devise a method of direct measurement of layer growth rate in a molecular beam apparatus which can be used while rotating the substrate during deposition.

Another object of the invention is to devise such a method that does not cause significant damage to the substrate during measurement of the growth rate.

SUMMARY OF THE INVENTION

These objects of the invention and other objects, features and advantages to become apparent as the specification progresses are accomplished by the invention according to which, briefly stated, a light source with appropriate optics focusses light on the wafer surface during deposition, while a nearby collector is biased to collect photoemitted electrons from the growing surface. A pico-ammeter can be used to convert the small oscillatory current detected to a substantial voltage signal which can be recorded or processed by computer or other suitable device. The light beam must contain power at energies close to or greater than the energy of the photoemission threshold. The detected photoemitted electron signal has an oscillatory component occurring due to the growth of epitaxial layers. This oscillation has frequency $1/\tau$ where $\tau$ is the monolayer accumulation time.

These and further constructional and operational characteristics of the invention will be more evident from the detailed description given hereinafter with reference to the figures of the accompanying drawings which illustrate preferred embodiments and alternatives by way of non-limiting examples.

BRIEF DESCRIPTION OF THE DRAWINGS

FIG. 3 is a plot of observed current as a function of time for a growth rate of 0.25 monolayers/second.

FIG. 4 is a plot of observed current as a function of time same growth rate of FIG. 3 but with higher gain.

FIG. 5 is a plot of observed current as a function of time for a growth rate of 0.4 monolayers/second with the gain the same as in FIG. 4.

GLOSSARY

The following is a glossary of terms, elements, and structural members as referenced and employed in the present invention.

10—molecular beam epitaxy apparatus
12—substrate holder
14—substrate
16, 18—furnaces
20—source of light
22—optics
24—power supply
26—window
28—light beam
30—collector
32—source of voltage
34—insulated feedthrough
36—coaxial collector
40—current detector
42—regulated DC power supply
44—rotating beam chopper
46—phase sensitive detector

DETAILED DESCRIPTION OF THE PREFERRED EMBODIMENTS

Figure 1:
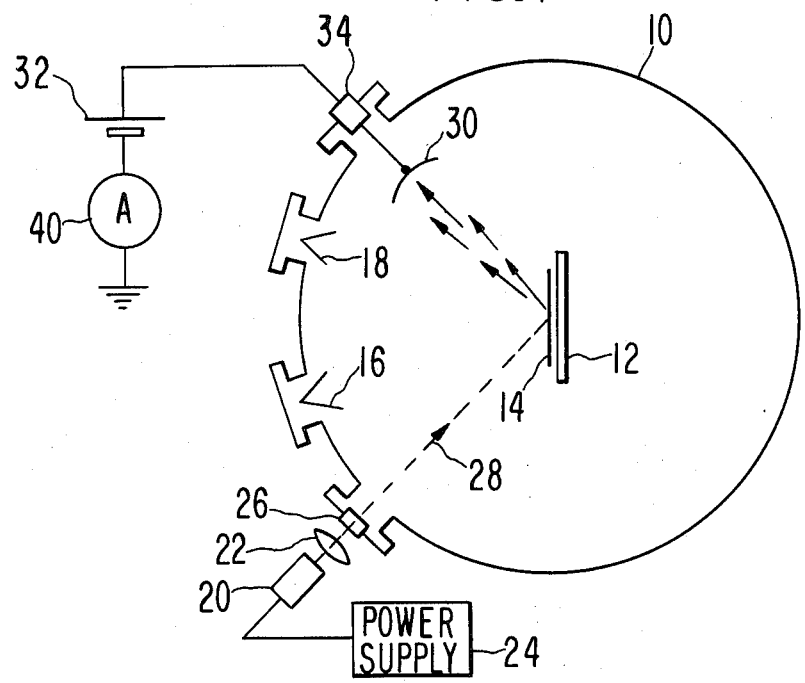
FIG. 1 is a schematic diagram of the apparatus according to the invention.

Referring now to the drawings wherein reference numerals are used to designate parts throughout the various figures thereof, there is shown in FIG. 1 a schematic diagram of the apparatus according to the invention. A molecular beam epitaxy apparatus of the prior art 10, such as a Varian Gen II MBE System, includes a substrate holder 12 for holding the substrate 14 on which the film is deposited by molecular beams from furnaces 16, 18. The deposition takes place in a vacuum environment. The measuring apparatus of the invention includes a source of light 20, suitable optics 22, such a quartz lenses for focussing the light beam on the wafer surface, a power supply 24 and a window 26 for passing the light into the vacuum chamber of the molecular beam apparatus 10. The window 26 used in one embodiment of the invention was made of sapphire. These elements form a beam of light 28 which makes a small spot of light on the surface of the film being deposited on the substrate 12. The light must be of sufficient energy to cause the photoemission of electrons from the surface of the film. A collector 30 is located so as to be in a position to collect photoemitted electrons and is biased with a source of voltage 32 at about 200 volts to enhance the collection of the electrons. The collector 30 is connected through an insulated feedthrough 34 to the electronics outside the vacuum.

A means for detecting the current of photoemitted electrons, such as a pico-ammeter 40, is connected to suitable display or recording equipment for analysis of the current. The current is seen to rise and fall periodically with time, the period corresponding to the time to form a molecular layer of the film. Molecular layers can thereby be counted as they form, permitting control of the thickness of the film to within a molecular layer.

Figure 2:
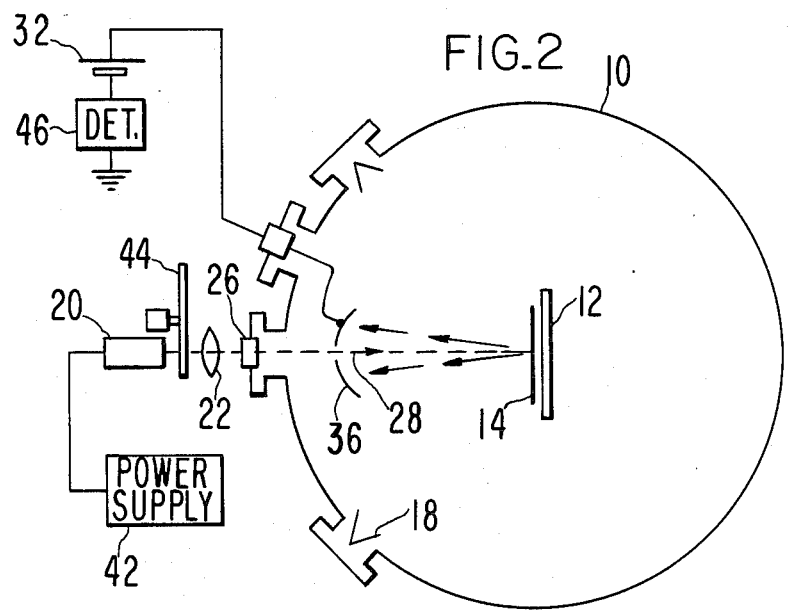
FIG. 2 is a schematic diagram of an alternate embodiment of the apparatus according to the invention.

With this apparatus and method, no orientation of the wafer with respect to the photon beam is required. In particular, a photon beam normally incident on the surface, as shown in the alternate embodiment of FIG. 2, with a coaxial electron collector 36 are particularly advantageous. Such an arrangement cannot have any rotational orientation dependence of the wafer in the photoemission yield and, hence, allows the wafer to be rotated while the measurement is being made.

A source of light which has proved workable during tests of the invention is a 45 W hydrogen/deuterium UV lamp. Typical spectral density curves for such lamps indicate roughly uniform power density with the absence of sharp lines in the range of wavelengths from 190 nm to 240 nm. The precise pattern of UV illumination on the wafer was not determined although from tests made out of the system it appeared that an area comparable to the two inch substrate would receive some light from the lamp. Improvements were made in the stability of the power emitted from the UV lamp. Specifically, a regulated DC power supply 42 was used to drive the hydrogen/deuterium lamp. This improved the signal to noise ratio considerably since noise in the lamp intensity directly couples to become noise on the signal.

The incident power of the light at the wafer in the wavelength range between the short wavelength cutoff of the window transmittance and the approximate photoemission threshold (190 nm to 225 nm) was estimated to be about 5 $\mu$w. This would correspond to a quantum efficiency of about 0.2% which is in reasonable agreement with previous measurements on clean GaAs surfaces. The collected current level was observed to be several nanoamperes. This current level slowly degraded with time as the inside of the window became coated with a thin layer of arsenic.

Further improvements were made by chopping the light beam with a rotating beam chopper 44 at about 300 Hz and synchronously detecting the signal with a phase sensitive detector 46. This modification helps reduce the influence of thermionic noise currents generated by the high temperature furnaces. Since such currents are not synchronous with the chopped light source they are effectively filtered using phase sensitive detection.

Examples of photoemission oscillation data recorded using the new scheme are shown in FIG. 3. The results reported here were obtained during the growth of GaAs layers on (100) oriented semi-insulating undoped wafers under "standard" growth conditions. Specifically, the substrate temperature during growth was held at 580°-590° C. as measured by an optical pyrometer. As is required for the growth of GaAs, a continuous flux of molecular arsenic was incident on the wafer whenever it was brought to elevated temperature. The fluxes of Ga and $As_4$ were measured by rotating an ionization gauge into the growth position and noting the beam equivalent pressure from each source. Typical ratios of the arsenic beam pressure to that of the gallium beam were about 17:1. The growth rate of the film was controlled by fixing the Ga cell temperature. For different layers, the rate varied from 0.2 to 0.5 monolayers/second. Here, one monolayer is about 0.282 nm.

In FIG. 3, the photoemitted current for a growth rate of 0.25 monolayers/sec (ml/s) is shown on an absolute scale, and the increase in signal when the gallium shutter is opened is seen to be $\approx 15\%$, with oscillation observed on top of this. The flux of gallium might be expected to cause a decrease in the photoemission threshold energy and consequently an increase in collected current due to the higher fraction of the surface covered by the more electropositive gallium atoms. It is interesting to note that under these conditions the RHEED pattern shows no substantial change. The near threshold photoemission signal, therefore, appears to be more sensitive than the observed RHEED pattern to changes in Ga surface coverage.

FIG. 4 shows the oscillations more clearly; it was recorded at higher gain. FIG. 5 shows oscillations due to a higher growth rate, 0.4 ml/s, recorded at the same gain as in FIG. 4. The oscillations are clear and distinct.

The magnitude of the oscillating current as a fraction of the overall photoemission current was in the range 0.5 to 1.0%. One interpretation of this is in terms of the average oscillatory change in the photoemission threshold energy. Assuming the electron energy distribution curve is roughly flat up to the window cutoff wavelength, the oscillation depth implies a threshold energy of 5 to 10 meV. In order to establish the oscillating signal to be a measure of the GaAs growth rate, a detailed comparison between photoemission and RHEED oscillations was undertaken. Oscillation frequencies were determined from the average of the first six periods of both signals at three different growth rates. Because of large variations in the uniformity of deposition and uncertainty of the illumination pattern, it was not clear that RHEED and photoemission measurements were being made on the same substrate areas and precise agreement between the measured photoemission and RHEED oscillation frequencies was not seen. However, it is clear that the measured photoemission frequencies are within the range of probable growth rates present on the wafer as measured by RHEED. Furthermore, all three sets of measurements are characterized by similar slopes indicating a common dependence on the vaporization rate of gallium from the effusion cell.

A more detailed analysis of the oscillating signal reveals that the "phase" relationship between the photoemitted current and the number of GaAs layers accumulated. Immediately after growth was initiated, the photoemission signal was dominated by the relaxation of the surface to the condition of increased gallium coverage. The more subtle oscillatory behavior was subsequently discernable and, using the growth rate inferred from the first several oscillations, the phase relative to the accumulated number of monolayers can be determined. Measurements were made under a variety of arsenic fluxes that correspond to As:Ga flux ratios of 15:1 to 40:1. In each case, the first observable minimum corresponded to the accumulation of $1.55 \pm 0.05$ monolayers. We estimate the uncorrected measurement error to be less than 3% of this value. This suggests that maxima in the observed oscillations correspond to integral values of monolayer accumulation and minima to half integral values.

These results contrast interestingly to studies of RHEED intensity oscillations, which are attributed to GaAs growth at monolayer terrace edges, either through diffuse scattering from monolayer terrace edges or Bragg-type diffraction effects. It has also been found that the phase of the oscillating signal may exhibit a complicated dependence on the physical geometry chosen. If the azimuthal and incident angles of the electron beam relative to the crystal surface are chosen properly, a bright spot due to specular reflection of the electron beam from the surface is observed. The bright spot becomes dim and diffuse at half integral layers and relatively bright and sharp at integral values of layer accumulation. At integral monolayer coverages, the surface would consist of many small islands of monolayers of GaAs above the previously accumulated layers.

The photoemission oscillations observed here could result from growth induced changes in the ionization energy or in the density of electronic states near the valence band edge. A reduction of the ionization energy would result in a large fraction of the incident photons being able to excite electrons above the photoemission threshold. An increase in the density of states near the valence band edge would provide more electrons capable of being photoemitted by the incident light beam. Of course, both phenomena could occur together. The bias on the collector plate is so large that the work function of the collector itself is unimportant; all emitted electrons accelerated by the collecting field will contribute to the photoemitted current. Therefore, band bending effects which might give rise to the measured contact potential difference would not necessarily change the photoemission threshold. This is principally so because the Fermi energy at the surface can be located at a particular energy in mid-gap due to a relatively small density of states, but we still require significant photoemission current to arise from valence band states.

The density of states on the (100) surface of GaAs, for various reconstructions of the surface, has been studied by a number of groups using Angle Resolved Photo-Emission Spectroscopy (ARPES). (See: Larsen et al, *J. Phys.*, C12, p.L869, 1979; Larsen et al, *Phys. Rev.*, B26, p. 3222, 1982; Chiang et al., *Phys. Rev.*, B27, p.4770, 1983; Svensson et al., *J. Vac. Sci. Technol.*, B2, p.235, 1984). In those experiments, surfaces were prepared by MBE, their reconstruction pattern observed by RHEED, and then cooled with the surface pattern maintained and transferred within the same vacuum system to the ARPES apparatus. As we have noted above, the energy integrated near threshold photoemission current for the same surface reconstruction varied considerably depending on parameters expected to affect the arsenic coverage. Samples cooled in an arsenic flux such that the surface reconstruction remains the same will undoubtably have arsenic coverages that depend on the cooling protocol and which may give rise to considerably different integrated photoemission currents than those obtained at high temperatures (600° C.) under a surface stabilized by an arsenic flux. It is therefore somewhat questionable what can be inferred from the density of states given by the ARPES measurements in the way of an explanation of the underlying mechanism leading to the oscillating photoemission signal. Qualitatively though, the existence of a considerable density of states localized at the surface can be proposed as a possible origin for the oscillating signal. In particular, surface states or resonances characteristic of the smooth surface occurring at the integral monolayer accumulations would be perturbed by the presence of small monolayer terraces at half integral accumulations. The in plane symmetry of the surface would be broken causing more spatial localization of the two-dimensional states. Such states would then be postulated to be more tightly bound and to reside further below the valence band maximum. This would result in a reduction of photoemitted electrons. The periodic modulation of surface smoothness on a monolayer scale that occurs during layer by layer growth would then lead to the observed modulation of the photoemitted current.

The influence of terrace edges on the ionization energy could result from several mechanisms. However, it has been generally observed that an increased density of steep edges causes a decrease in ionization energy in the case of metals, silicon, and cleaved (110) GaAs. (See: Besocke et al, *Phys. Rev.*, B8, p.4597, 1973; Besocke et al., *Surf. Sci.*, 53, p. 351, 1975; Krueger et al., *Surf. Sci.*, 99, p.157, 1980; Monch et al., *J. Vac. Sci. Technol.*, 16, p.1238, 1979). If this is also true on growing (100) surfaces, the increased terrace edge density at half integral monolayer accumulations would lead to a higher photoemission current which is exactly the opposite of what is observed. It is possible that the nature of the bridging and dangling bonds and the reconstruction of the polar (100) surfaces encourages growth in such a way that exposed terrace edges have higher ionization energies. Another consequence of terrace edge growth could cause changes in the ionization energy and directly lead to the prediction of oscillatory photoemission signals of the correct phase. Since gallium atoms on the surface are relatively loosely bound and mobile until they incorporate into a monolayer at a terrace edge, the increased density of terrace edges at half integral monolayer accumulations would directly lead to decreased free gallium atom surface lifetime. If free gallium atoms on the surface are more effective in reducing the ionization energy than those incorporated at terrace edges, increased photoemission would be observed when the density of terrace edges is the minimum, namely at integral values of monolayer accumulation. The kinetics of the $As_4$ is, in fact, thought to favor reaction with adjacent gallium atoms which are more likely to be available at terrace edges. This would result in more rapid arsenic coverage of gallium atoms incorporated in a terrace than those on the free surface, and the reduction of dipoles favoring photoemission.

Thus, there would appear to be several plausible explanations for the photoemission oscillations that we have observed. First, they may depend upon variations in surface state densities located just below the valence band edge. Evidence both for and against this hypothesis has been presented, but as observed above, it is not clear that these data have direct applicability to the growing surface. Second, we have postulated a mechanism in which the terrace edges may be considered to "getter" the deposited Ga and therefore indirectly affect the surface dipole. Also, the terrace edges may directly influence the surface dipole, but in that case we have shown that it would be necessary to assume that they do so in the opposite sense to previous observations on various non-polar surfaces. We cannot, at present, discriminate between these possibilities further except to note that the first case would probably be considered less viable if, as we suspect, the phenomenon turns out to be more general to other surfaces. In the future, we anticipate this technique as well as obvious application to growth rate monitoring will be greatly enhanced by the incorporation of a tunable monochromatic light source which may allow significantly more information to be obtained about the dynamics of the growing surface.

It is still thought that improved oscillation characteristics, in particular improved signal to noise and duration of the oscillatory signal, will result from improved characteristics of the UV source. A more perfectly focussed beam will sample a smaller area of the growing surface and signal damping due to inhomogeneities in the growth rates detected will be reduced. A heated window will prevent accumulation of arsenic on the window which degrades the illumination of the growing layer. Also a narrowband source, such as a laser source, will result in better modulation depth of the signal since a larger fraction of the photoemitted electrons will be sensitive to the small ionization energy changes that give rise to the signal.

Lasers in fact provide such high intensity light that multiphoton photoemission is possible. A system for observing two photon photoemission oscillations would look similar to FIG. 2 with the light source tuned to near or just above half the photoemission energy. Likewise, multiple photon processes would require tuning to near 1/n times the photemission energy for n photon processes.

The apparatus according to the invention can be used to provide feedback to a computer controlling source shutters to effect precise control over the number of layers of a given material deposited, and do so even with the substrate rotating. Large area wafers can therefore be grown with good layer thickness control. Direct measurement and control of the growth rate provides advantages of adding a capability to vary the outputs of the furnaces with time during the deposition to produce more complex and higher quality films.

This invention is not limited to the preferred embodiment and alternatives heretofore described, to which variations and improvements may be made including mechanically and electrically equivalent modifications to component parts, without departing from the scope of protection of the present patent and true spirit of the invention, the characteristics of which are summarized in the following claims.

What is claimed is:

1. A method of measurement of the growth rate of a film being grown on a substrate in a molecular beam epitaxy apparatus, the method comprising the steps of:
   (a) illuminating the growing film with light of energy sufficient to cause photoemission of electrons,
   (b) collecting the photoemitted electrons on a collector,
   (c) detecting the photoemitted electron current to said collector as a function of time, and
   (d) analyzing oscillations of the photoemitted electron current to the collector to count molecular layers grown as a function of time.

2. The method of claim 1 wherein said step (a) includes illuminating the growing film with light from a UV source.

3. The method of claim 2 wherein said step (a) includes focussing the UV source light with a lens onto a spot on the growing film.

4. The method of claim 1 wherein said step (a) includes illuminating the growing film with a laser.

5. The method of claim 4 wherein the laser has photon energy less than that required for single photon photoemission.

6. The method of claim 3 wherein said step (a) includes illumination of the growing film through a chopper and said step (c) includes detecting the photoemitted electron current by phase sensitive detection.

7. The method of claim 4 wherein said step (a) includes illumination of the growing film through a chopper and said step (c) includes detecting the photoemitted electron current by phase sensitive detection.

8. The method of claims 6 or 7 wherein the steps (a), (b) and (c) are performed while simultaneously rotating the substrate on which the film is being grown.

9. The method of claim 8 wherein in step (a) light from a source passes into the interior of the molecular beam apparatus through a heated window at a temperature sufficient to prevent the accumulation of a deposition.

10. The method of claim 1 wherein the step (a) includes illuminating the growing film from a source of electromagnetic energy by having energy close to or greater than the energy of the photoemission threshold of said film being grown.

11. The method of claim 2 wherein the UV source is a hydrogen/deuterium UV lamp powered by a regulated DC power supply.

12. Apparatus for measuring the growth rate of a film being grown on a substrate in a molecular beam apparatus in a vacuum environment, comprising:
   a source of light illuminating the film, the light being of sufficient energy to cause photoemission of electrons from the film being grown,
   a collector means for collecting electrons photoemitted from the film due to illumination by said source of light, and
   means for detecting a current of photoemitted electrons to said collector means as a function of time.

13. The apparatus of claim 12 including a heated window between the source of light and the film being illuminated, said heated window forming a portion of a wall containing the vacuum environment, said window being heated to temperature high enough to prevent deposition on an inside surface of said window.

14. The apparatus of claim 13 including means for chopping light from said source of light and wherein said means for detecting includes phase sensitive means for detecting photoelectrons caused by chopped light.

15. The apparatus of claim 13 wherein said source of light is a hydrogen/deuterium UV lamp with lens means to focus the light in a spot on the growing film, said lamp being powered by a regulated DC source.

16. The apparatus of claim 13 wherein said source of light is a laser.

17. The apparatus of claim 16 comprising means for operating said laser at a photon energy less than that required for single photon photoemission.

18. The apparatus of claim 15 including means for chopping light from said source of light and wherein said means for detecting includes phase sensitive means for detecting photoelectrons caused by chopped light.

19. The apparatus of claim 16 including means for chopping light from said source of light and wherein said means for detecting includes phase sensitive means for detecting photoelectrons caused by chopped light.

20. The apparatus of claims 18 or 19 comprising means for directing light from said source of light perpendicular to the surface of the growing film.

21. The apparatus of claim 12 wherein said collector means is concentric with the light from said source of light.

22. The apparatus of claim 19 wherein light from said source of light is incident perpendicular to the surface of the growing film and wherein said collector means is concentric with the light from said source of light.

23. Apparatus for growing layers of uniform and precisely controllable thickness comprising:
(a) a molecular beam device for growing layers on a substrate, including shutters to control input gas sources and means for rotating said substrate during growth in a vacuum environment;
(b) a source of light for illuminating said substrate during rotation with a light of sufficient energy to induce emissions of electrons from the film being grown on the surface of said substrate;
(c) a collector means for collecting electrons emitted from the film being grown;
(d) means for displaying the collected electron current as a function of time to provide a measure of the rate of growth of said layers while said layers are being grown.

24. The apparatus of claim 23 comprising feedback to a computer for controlling said input gas shutters to effect precise thickness control.

* * * * *